United States Patent [19]

Misra et al.

[11] Patent Number: 5,309,374
[45] Date of Patent: May 3, 1994

[54] ACOUSTIC AND VIDEO IMAGING SYSTEM FOR QUALITY DETERMINATION OF AGRICULTURAL PRODUCTS

[75] Inventors: Manjit K. Misra; Yuh-Yuan Shyy, both of Ames, Iowa

[73] Assignee: Iowa State University Research Foundation, Inc., Ames, Iowa

[21] Appl. No.: 924,195

[22] Filed: Aug. 3, 1992

[51] Int. Cl.$^5$ .............................................. G06F 15/20
[52] U.S. Cl. ................................................... 364/552
[58] Field of Search ...................... 356/407; 364/552; 382/1, 8

[56] References Cited

U.S. PATENT DOCUMENTS

| | | | |
|---|---|---|---|
| 4,350,442 | 9/1982 | Arild et al. ............................. | 356/51 |
| 4,463,608 | 8/1984 | Takeuchi et al. ...................... | 73/606 |
| 4,518,992 | 5/1985 | Kessler et al. ....................... | 358/112 |
| 4,586,613 | 5/1986 | Horii ..................................... | 209/556 |
| 4,741,042 | 4/1988 | Throop et al. ......................... | 382/1 |
| 4,856,336 | 8/1989 | Falkevich et al. ..................... | 73/598 |
| 4,926,872 | 5/1990 | Brock-Fisher et al. ......... | 128/661.01 |
| 4,974,211 | 11/1990 | Corl ..................................... | 367/7 |

OTHER PUBLICATIONS

"Computer Vision For Soybeans"; Manjit K. Misra et al.; ASAE/CSAE Summer Meeting presentation Jun. 25-28, 1989; Paper No. 89-3001.
"Color Image Analysis For Soybean Quality Determination"; Yuh-Yuan Shyy et al.; ASAE/CSAE Winter Meeting presentation Dec. 12-15, 1989; Paper No. 89-3572.
"A Prototype For Acoustic Determination of Soybean Quality"; Yuh-Yuan Shyy et al; ASAE Winter Meeting presentation Dec. 12-15, 1989; Paper No. 89-6608.
"Acoustic Properties of Soybeans"; M. K. Misra et al.; ASAE vol. 33, No. 2; pp. 671-677, Mar.-Apr., 1990.

Primary Examiner—Edward R. Cosimano
Attorney, Agent, or Firm—Flehr, Hohbach, Test, Albritton & Herbert

[57] ABSTRACT

A flexible system for determining the quality of agricultural products based on characteristics such as, for example, mass, shape, hardness, size, color and surface texture is disclosed herein. The quality determination apparatus includes a feeder assembly for sequentially dropping individual product samples upon an impact transducer arrangement. The impact transducer generates transducer signals indicative of the physical characteristics of each product sample. In addition, an imaging device operates to synthesize a digital image representation of each product sample. The transducer signal and digital image representation corresponding to each product are analyzed so as to determine the appropriate degree of quality to be associated therewith.

22 Claims, 13 Drawing Sheets

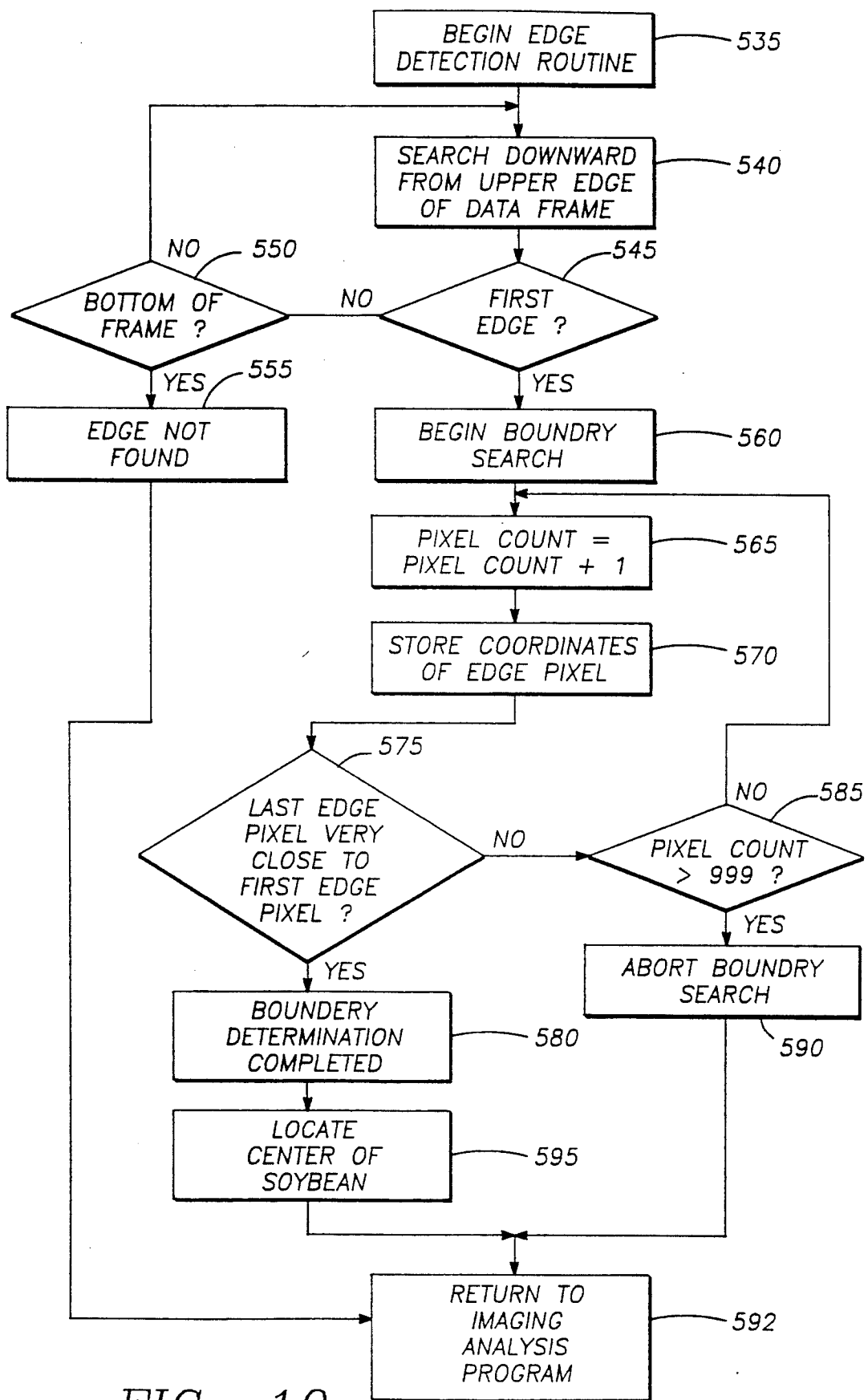
FIG.—10

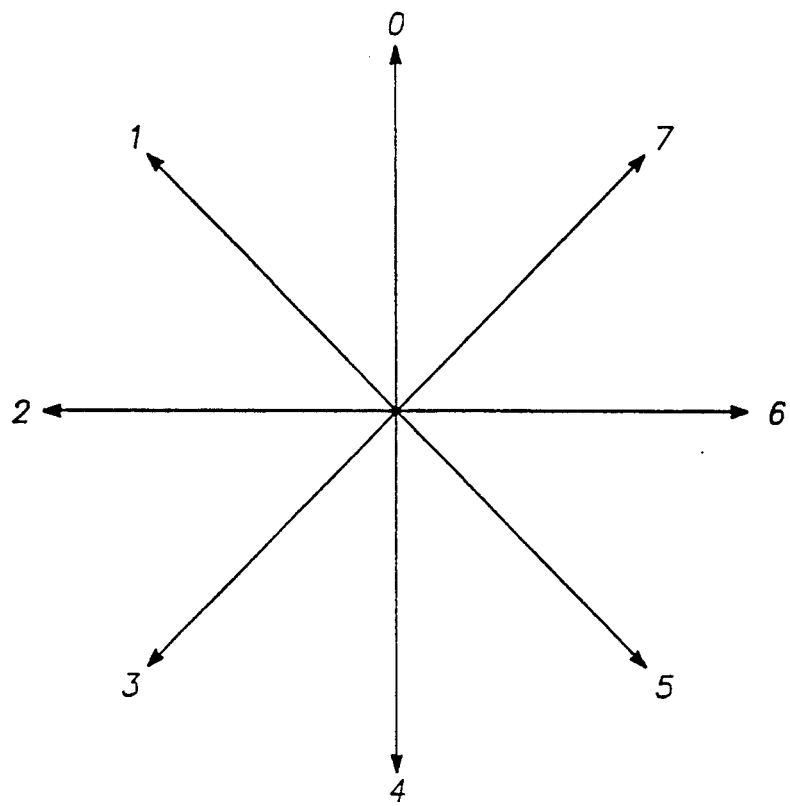
FIG.—11
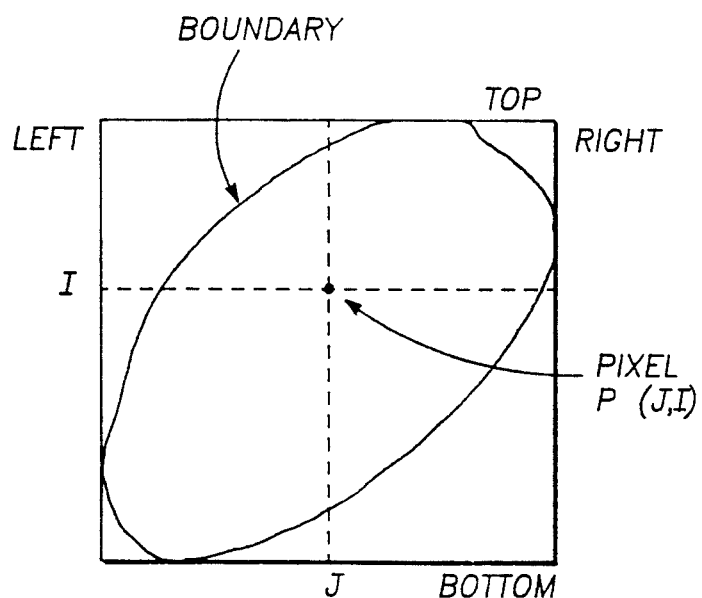
FIG.—13

ACOUSTIC AND VIDEO IMAGING SYSTEM FOR QUALITY DETERMINATION OF AGRICULTURAL PRODUCTS

The U.S. government has certain rights in the invention pursuant to contract No. ITA 87-02 between the U.S. Department of Commerce and Iowa State University.

The present invention relates generally to quality control of agricultural products, and particularly to quality control techniques involving acoustical and video signal processing.

BACKGROUND OF THE INVENTION

Interest in using image processing to aid in quality control and grading for a variety of agricultural products has recently become a subject of considerable research. In particular, efforts have been made to use computer-assisted imaging techniques to facilitate recognition of defective agricultural products. Computer imaging systems generally include a color video camera connected to a frame grabber. The frame grabber digitizes the image provided by the camera and relays the image information to a computer. Analysis of the digital image information may then be performed using a variety of techniques. In particular, the potential has been shown to discriminate between crop seeds and certain common contaminants based on image parameters such as area, perimeter, aspect ratio, shape factor, and the like. Other applications have involved classification of diploid and tetraploid ryegrass seeds, and orientation determination of vegetables using grey-level intensity gradients and syntactic pattern recognition techniques.

By way of example, a computer vision system for determining soybean quality based on size and shape parameters has been developed (see Misra, et al., *Computer Vision for Soybeans*, presented at the 1989 International Summer Meeting of American Society of Agricultural Engineers and Canadian Society of Agricultural Engineering, Paper No. 89-3001). Images of a soybean are first captured using a charge-coupled device (CCD) camera and digitized by a frame grabber. The image processing sequence is initiated by determining an outline of the soybean under analysis by searching for contrasts between the portions of the image corresponding to the background and to the soybean itself. A routine is then used to fit an ellipse to the outline, since acceptably healthy soybeans were found to be generally elliptical in shape. While capable of successfully discriminating between soybeans having varying degrees of quality, it is believed that the efficiency of the machine vision system described above could be improved by modification of particular aspects of the disclosed image processing sequence.

Concurrent with the development of the image processing techniques described above, efforts have been made to develop acoustical methods of analysis based on the transmittance, absorption or reflection of sound waves by agricultural products. These techniques are based on the realization that even minor changes in the structure or health of a product will result in variation of its acoustic properties. Such variations can be quantitatively evaluated by analyzing the frequency components of the sound wave. Frequency data is generally processed using analytic procedures such as the Fast Fourier Transform (FFT), which can be performed to identify the ways in which selected frequencies are absorbed, transmitted or reflected by the product being investigated. These frequency response characteristics can be correlated with various physical properties of the product related to quality.

In the particular case of the analysis of soybeans, at least two types of acoustical methods have been investigated (see, e.g., Misra, et al., *Acoustic Properties of Soybeans*, Transaction of the American Society of Agricultural Engineers, 33(2):671-677). In a first, or "acoustic transmission" technique, a soybean kernel is placed between input and receiving transducers where the former introduces an acoustic impulse to the kernel and the latter records the wave transmitted through the kernel. Both waves, the input and the transmitted, can be digitally recorded and analyzed by a Fast Fourier Transform. The two spectra can then be compared, usually by dividing the transmitted wave by the input wave to identify frequencies that are preferentially absorbed by the kernel so as to provide an indication of kernel quality. Specifically, quality may be determined by analyzing the differences in the absorption spectra of a "good" or reference soybean and the soybean under scrutiny. Unfortunately, the acoustic transmission spectra of an ideal soybean has been found to be difficult to describe mathematically. Accordingly, correlation between the transmission spectra and size or mass of the soybean has not been possible, thus precluding effective quality determination. Moreover, the placement of each soybean between the transducers has been found to be a relatively slow process.

A second, or "impact-force" method of acoustical characterization of soybeans involves dropping soybeans through a guide tube coupled to a piezoelectric force transducer. An impact signal generated by the transducer is routed to a digitizer and then to a computer. A computer program then operates to derive the frequency spectra of the impact signal by using an FFT algorithm. As in the acoustic transmission technique, correlation of the frequency spectra of the impact signal with a set of quality parameters requires the spectra to be mathematically described. Such a description could be effectuated through, for example, polynomial approximations, sine functions, or simple Bessel functions. Although the impact-force method has been shown to allow for faster determination of soybean quality, the frequency-domain procedure outlined above is relatively computationally intensive. That is, the procedure requires an initial FFT conversion of the impact signal into the frequency domain and a subsequent parameterization of the spectral characteristics so obtained. It is thus believed that a time-domain method for analyzing the transducer signal produced by an impact-force apparatus would allow for a more rapid determination of the quality of an agricultural product being investigated.

While image processing and acoustical techniques have each been of separate assistance in determining the quality of agricultural products, a system incorporating both of these methodologies would allow for increased flexibility with respect to the criterion used for quality determination. For example, such an integrated system would allow a user to specify that a set of product characteristics derived from both the acoustical and video reals constitute the basis for acceptable quality.

OBJECTS OF THE INVENTION

It is an object of the present invention to provide a system for determining the quality of agricultural products in which is incorporated both image processing and acoustical techniques.

It is a further object of the present invention to provide such a quality determination system adapted to analyze agricultural products such as soybeans and the like.

SUMMARY OF THE INVENTION

The present invention addresses the need for a flexible system for determining the quality of agricultural products based on characteristics such as, for example, mass, hardness, shape, color and surface texture. The inventive quality determination apparatus includes a feeder assembly for sequentially dropping individual product samples upon an impact transducer arrangement. The impact transducer generates transducer signals indicative of particular physical characteristics of each product sample. In addition, an imaging device operates to synthesize a digital image representation of each product sample. The transducer signal and digital image representation corresponding to each product are then analyzed so as to determine the appropriate degree of quality to be associated therewith.

BRIEF DESCRIPTION OF THE DRAWINGS

Additional objects and features of the invention will be more readily apparent from the following detailed description and appended claims when taken in conjunction with the drawings, in which:

FIG. 10 is a flow chart summarizing the manner in which the edge of an image of an agricultural product sample is distinguished from the background of a digital image representation thereof.

FIG. 11 illustratively represents a set of eight direction vectors used in a boundary search operation performed in connection with the digital image analysis of each product sample.

FIG. 13 depicts the manner in which the texture, area and color of the surface of each soybean may be calculated using a pixel-by-pixel comparison and area normalization.

DESCRIPTION OF THE PREFERRED EMBODIMENT

Description of Mechanical Apparatus

Figure 1:
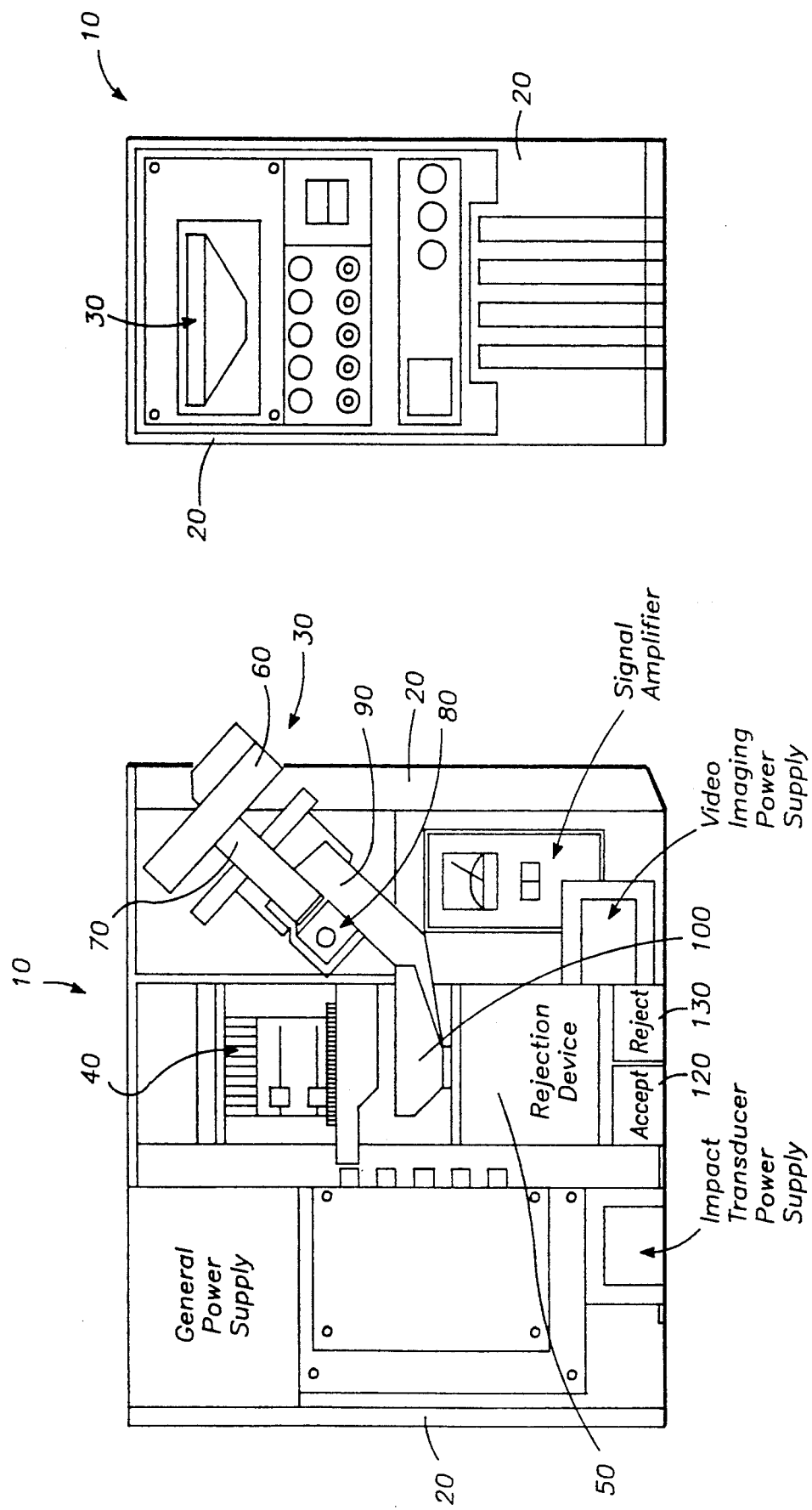
FIGS. 1a and 1b show a see-through side view and front view, respectively, of a preferred embodiment of the agricultural product quality determination system of the present invention.

Referring to FIGS. 1a and 1b, there are shown a see-through side view and a front view, respectively, of a preferred embodiment of the agricultural product quality determination system 10 of the present invention. The inventive system 10 is adapted to analyze relatively firm agricultural products, such as soybeans and various other varieties of beans and the like. Nonetheless, it is understood that the specific mechanical implementation of the system 10 depicted in FIG. 1 may be modified to accommodate analysis of agricultural products of varying size and firmness.

The quality determination system 10 is enclosed within a housing 20 and includes a drop tube feeder apparatus 30, a video imaging device 40, and a quality control rejection device 50. As is described in detail below, the soybeans or other agricultural products to be analyzed are loaded into a sample container 60 included within the feeder apparatus 30. A rotating disk (not shown in FIGS. 1A and 1B) within the sample container 60 allows one soybean at a time to slide down a drop tube 70 and fall upon an impact transducer 80. An acoustical impact signal generated by the transducer 80 is then digitized and routed to a computer (not shown) for analysis. Based on this analysis the quality of the soybean may be evaluated in terms of mass and hardness. The soybean is deflected by the transducer 80 into a U-channel trough 90, which guides the soybean to a holding bin 100.

The video imaging subsystem 40 operates to create a digital image representation of the soybean while it is confined in the holding bin 100. The digital image representation of the soybean is then processed so as to enable a determination of quality to be made on the basis of parameters such as lustre, color, shape and roughness. The inventive system 10 is designed such that a user may specify the extent to which each of the acoustical and image parameters mentioned above contributes to the criteria used in making an overall assessment of soybean quality. As shown in FIG. 1A, the rejection device 50 routes soybeans to either accepted bean bin 120 or rejected bean bin 130 from the holding chamber 100 in accordance with such a composite quality evaluation.

Figure 2:
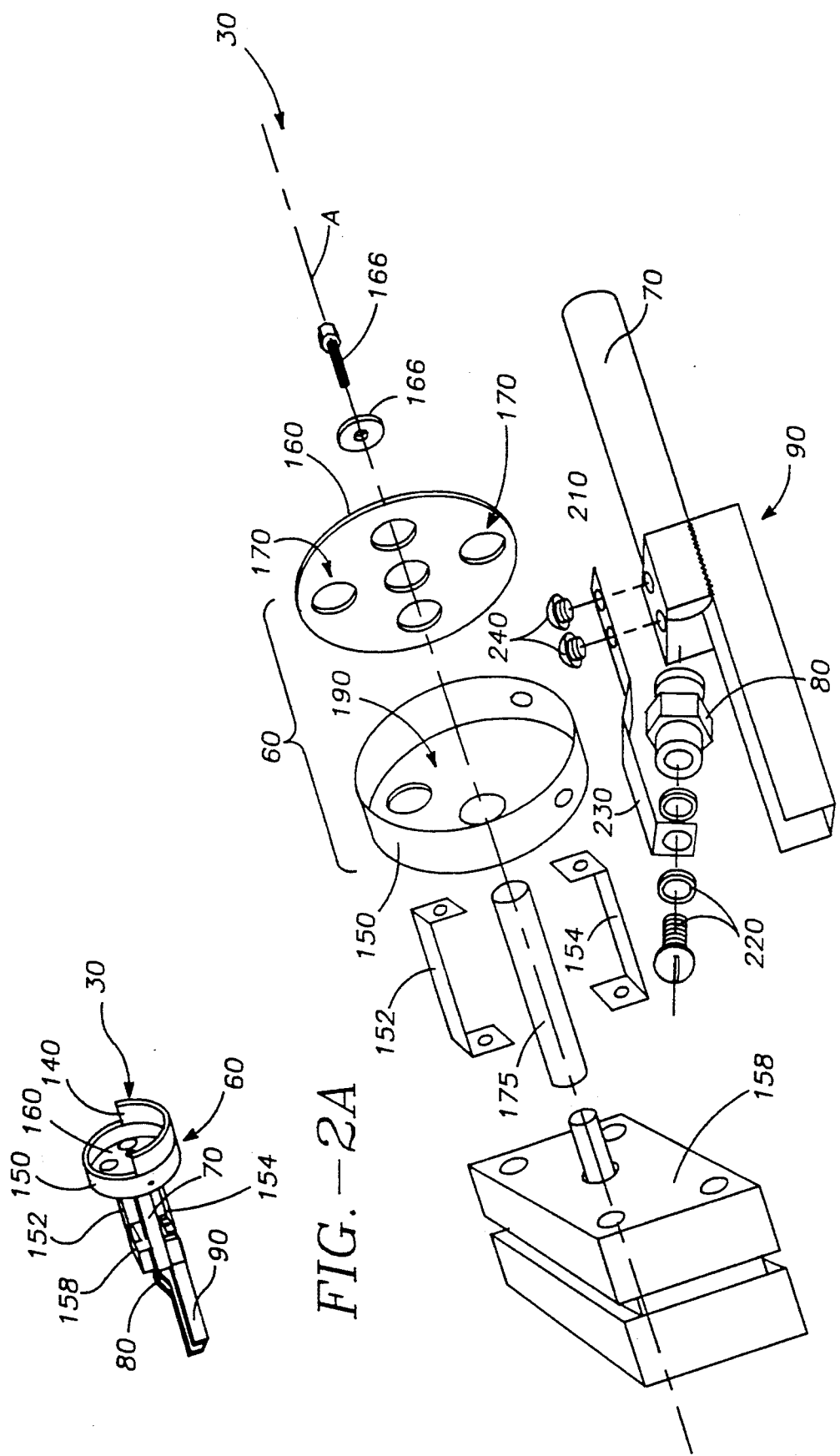
FIGS. 2a and 2b depict a drop tube feeder apparatus in greater detail as assembled, and as partially disassembled, respectively.

FIGS. 2A and 2B depict the drop tube feeder apparatus 30 in greater detail as assembled, and as partially disassembled, respectively. Referring to FIG. 2A, a flange 140 appended to a lower portion of the container 60 is designed to increase the number of number of soybeans which may be accommodated therein. That is, given the 45 degree orientation of the feeder apparatus 30 the soybeans loaded therein will tend to settle within the lower portion of the container 60. The flange 140 has been omitted from FIG. 2B for purposes of clarity. The sample container 60 further includes a cylindrical housing member 150 secured by first and second brackets 152 and 154 to a motor 158. A rotating disk 160 approximately 4 inches in diameter is positioned within housing member 150. As shown in FIG. 2B, the disk 160 defines a set of four holes 170 having diameters slightly larger than the diameter of the soybeans included within sample container 60. Consequently, the holes 170 will generally be less than 0.5 inches in diameter. The disk 160 is coupled by conventional hardware 166 to a drive shaft 175 of motor 158, thereby allowing easy interchange of disks when soybeans of a different diameter are loaded into the container 60.

As the disk 160 is rotated about an axis A by shaft 175, the cavities defined by each of the holes 170 and the portion of the housing 150 underlying the disk 160 will capture a soybean upon passing through the soybeans accumulated in the lower portion of the container 60. If the cavity corresponding to a particular hole 170 happens to capture more than a single soybean, gravity will tend to cause all but one to fall out as the cavity rotates to an upper portion of the container 60. In this way rotation of the disk 160 causes each of the holes 170 to periodically become aligned with a similarly dimensioned aperture 190 defined by an upper portion of the housing 150. During each such alignment a single soybean passes from the container 60 through aperture 190 into the drop tube 70, which is also aligned with the aperture 190. The disk 160 is rotated each time the acoustical and video data acquired for a particular soybean has been processed in a manner to be discussed below, and remains stationary during the intervening intervals. It has been found that the inventive system 10 is capable of processing at least one soybean per second, which corresponds to an average disk rotation rate of approximately 15 revolutions per minute.

Again referring to FIGS. 2A and 2B, the drop tube 70 is typically approximately 4 inches in length, is oriented at 45 degrees relative to vertical, and extends into a rectangular coupling member 210 of the U-channel trough 90. The impact transducer 80 is secured by hardware 220 to a third bracket 230, with the third bracket 230 being affixed to the coupling member 210 using hardware 240. The bracket 230 serves to position the impact transducer 80 such that soybeans falling from the drop tube 70 are deflected by the transducer 80 into the ¾" U-channel trough 90. The transducer 80 may be implemented with, for example, a conventional impact transducer manufactured by PCB Piezotronics of Depew, N.Y., part no. 208A02. Subsequent to deflection by the transducer 80, each soybean slides through the U-channel trough 90 into the holding bin 100.

Figure 3:
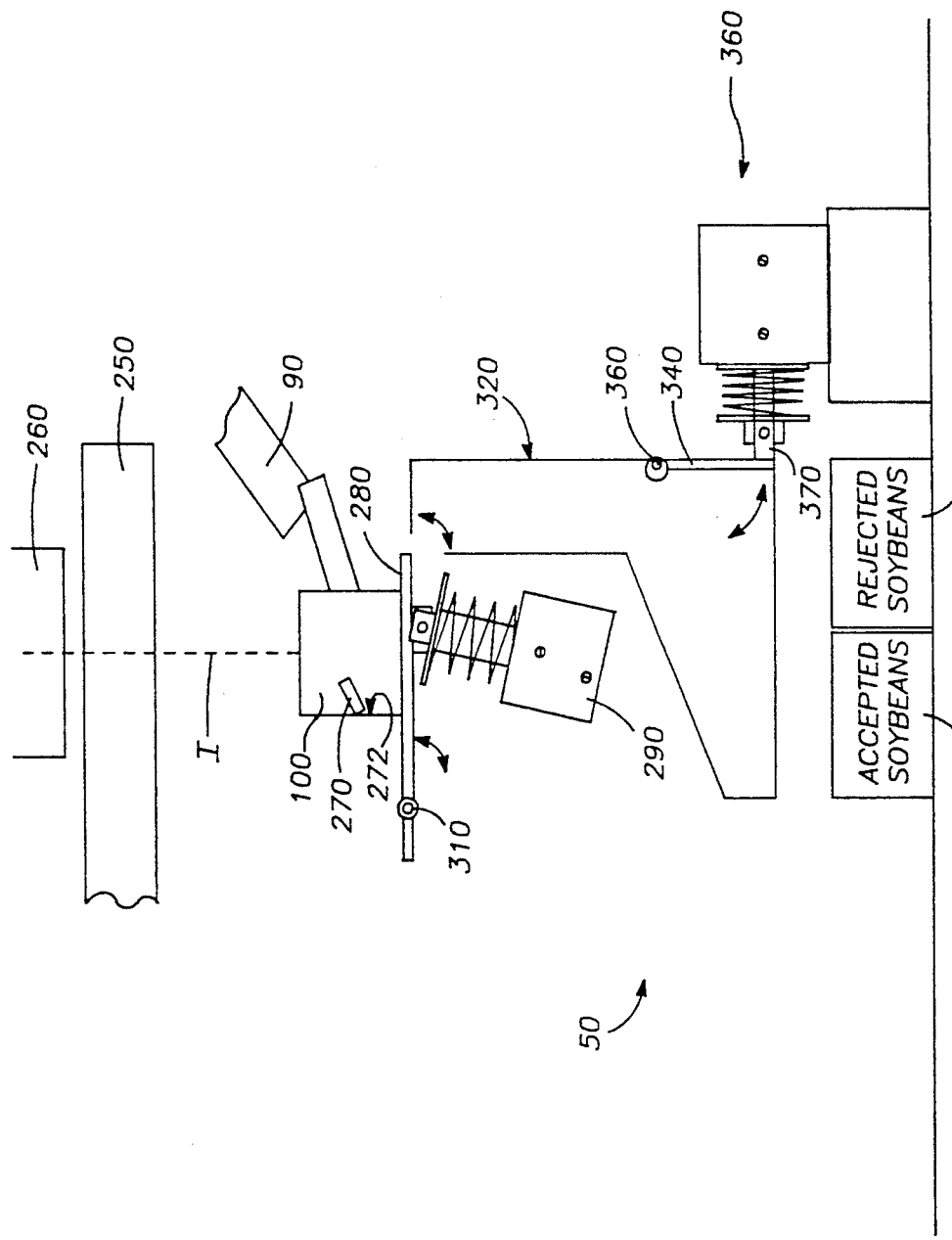
FIG. 3 shows a more detailed side view of an agricultural product holding bin and product rejection device.

FIG. 3 shows a more detailed side view of the holding bin 100 and rejection device 50. Also shown in FIG. 3 is U-shaped fluorescent lighting source 250 interposed between the holding bin 100 and a lens element 260 of the video imaging device 40. The imaging device 40 is designed to create a digital image representation of each soybean entering the holding bin 100 from the trough 90. Such an imaging system could be conventionally realized using an arrangement consisting of a camera, and a frame grabber. Preferably, however, the imaging device 40 will be implemented with an integrated unit similar to, for example, a conventional slide scanner. A slide scanner having suitable resolution is available from RasterOps Corp. of Santa Clara, Calif., as the "Expresso". The device produces either standard NTSC or PAL video output, and images can be captured by a computer using a frame grabber board.

Referring to FIG. 3, lens element 260 is in optical alignment with an image axis I, while the U-shaped lighting source 250 partially encircles the axis I. The lighting source 250 provides uniform illumination over the surface of soybeans within the holding bin 100, and may be implemented with, for example, a 110 Volt fluorescent tube. The imaging device 40 is triggered to create an image of the contents of the holding bin 100 following impact of a soybean upon the transducer 80. Again, the impact signal generated by the transducer 80 may be monitored to determine the precise time at which a soybean collides with the transducer 80. As is discussed more fully below, the present invention employs an object detection scheme to determine when a soybean enters the field of view of lens element 260 upon entering holding bin 100 after being deflected by the impact transducer 80. The object detection process is repeated until the imaging system 40 is successful in capturing an image of the soybean. Given that soybeans are generally yellow in color, in the presently preferred embodiment of the inventive system 10 the interior surfaces of the holding bin 100 are painted flat black in order to improve the contrst of the digital image representation.

As is shown in FIG. 3, a photocell 270 for determining soybean lustre (reflectivity) is mounted on an interior surface 272 of the holding bin 100. The photocell 270 will preferably be installed within a ¾" diameter tube oriented downward at 45 degrees relative to the bin surface 272. The photocell 270 is disposed to continuously provide an electrical signal indicative of the amount of radiant energy from the lighting source 250 reflected by the holding bin 100 and by any soybeans therein. Soybean reflectivity is determined by sampling the photocell signal, generally at a sampling rate of less than 1 MHz, during an interval immediately following generation of the impact signal. Between one and three hundred samples will typically be averaged and the result compared with a background photocell signal (i.e., the signal produced by photocell 270 when no soybeans are present within the holding bin 100). The results of this comparison are indicative of soybean reflectivity, and are stored in the memory of a host computer described below. The photocell 270 can be conventionally realized using, for example, a cadmium sulphide photocell, available from Radio Shack, Inc., part no. 276-116. Referring to FIG. 3, the holding bin 100 includes a hinged floor 280 coupled to a first solenoid 290. After an image of the soybean within the holding bin 100 has been created by the imaging device 40, solenoid 290 is actuated and operates to rotate floor 280 clockwise about hinge 310. The soybean resting on floor 280 then falls through chute 320 and either is collected by rejected soybean bin 130, or is deflected by a hinged arm 340 into accepted soybean bin 120. If the soybean has been determined to be of acceptable quality a second solenoid 360 having a shaft 370 coupled by an "O" ring (not shown) to hinged arm 340 operates to rotate arm 340 clockwise about hinge 360. The falling soybean is thereby deflected by arm 340 into accepted soybean bin 120. The first and second solenoids 290 and 360 then return the floor 280 and arm 340 to their respective initial positions.

Description of Computer and Interface

Figure 4:
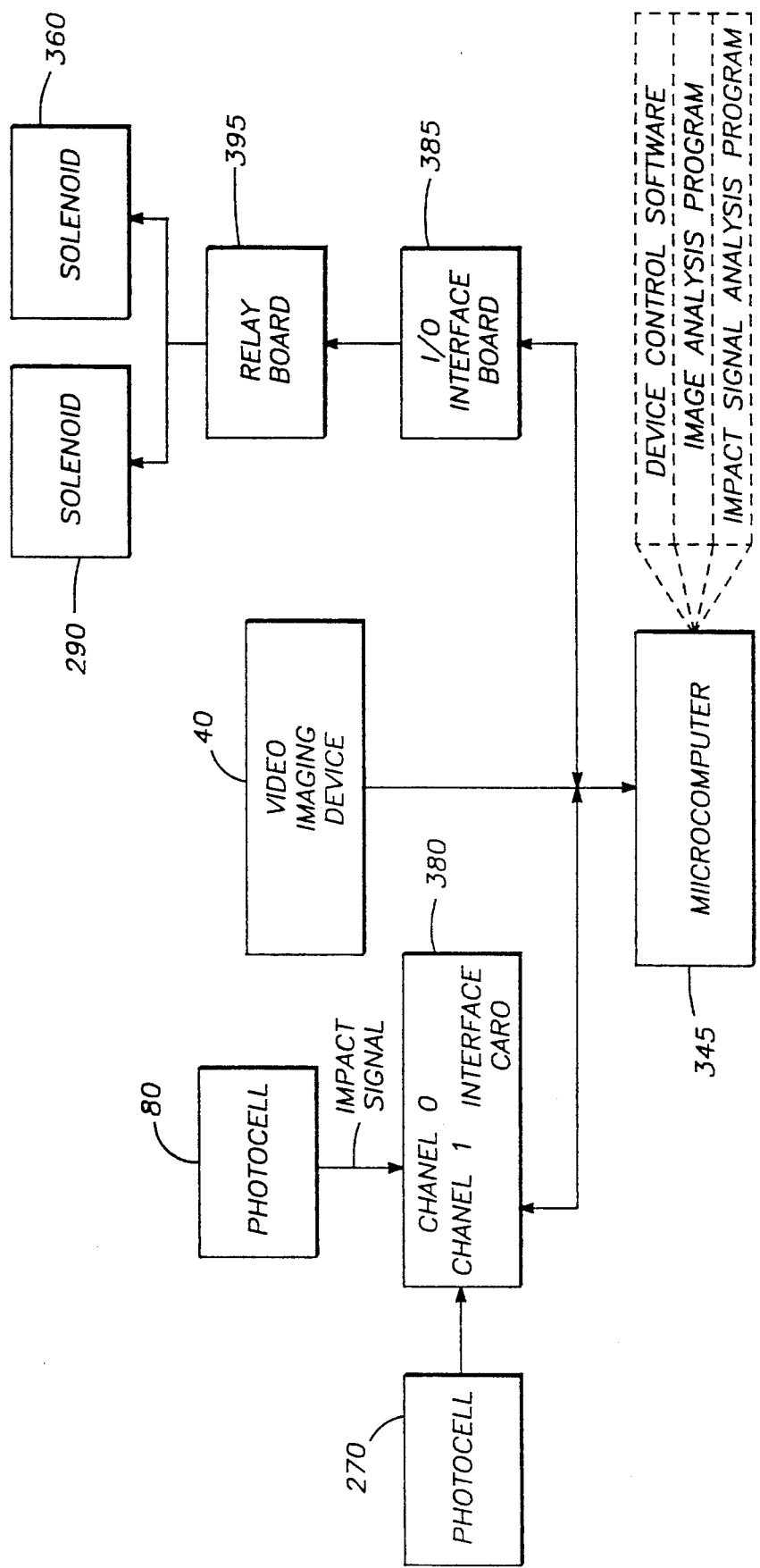
FIG. 4 provides a block-diagrammatic overview of the signal processing elements incorporated within the inventive agricultural product quality determination system.

FIG. 4 provides a block-diagrammatic overview of the signal processing elements incorporated within the inventive agricultural quality determination system 10.

General computing capability is provided by a Gateway 386-33 microcomputer 345 operative at 33 MHz. The Gateway 386-33 includes an IBM PC/AT compatible microcomputer based on an Intel 80386-33 processor together with an Intel 80387-33 math co-processor, and also was equipped with four megabytes of random access memory (RAM), disk drives, and a hard drive. When the imaging device 40 is conventionally implemented using a standard video camera, a Targa-16 color image capture board (frame grabber) having 512 kilobytes of static RAM enables the Gateway 386-33 to digitize electronic photographs from the camera. This enables display of the digital image representation synthesized by the imaging device 40 on an analog RGB monitor or an NTSC color video monitor. The captured images exhibited 512 (horizontal) by 483 (vertical) pixel resolution, with each pixel representing one of 32,768 displayable colors.

Referring to FIG. 4, a Keithly DAS-50-1M, A/D high speed interface card 380 for digitizing the impact and photocell signals is incorporated within the microcomputer. The Keithly DAS-50 provides a 1 MHz conversion rate, and is equipped with an on-board memory buffer for locally holding data until access is requested by a transfer command from the microcomputer. The impact signal from transducer 80 is routed to channel #0 of the interface card 380, while the signal from the photocell 270 is received by channel #1. In order to access the interface card 380, a series of ASCII commands are sent by software resident within the microcomputer in accordance with the syntax for the card 380. Specifically, a procedure written in the Pascal computer language linked with an assembly language subroutine has been written to read registers of the interface card 380, and to control the transfer of information from the interface card data buffer.

Again referring to FIG. 4, the first and second solenoids 290 and 360 are controlled by the microcomputer via a PIO-12 input/output board 385 in conjunction with an ERA-01 8-channel relay board 395. A group of device functions for controlling the solenoids 290 and 360 have been written using Microsoft Macro-Assembler.

Analysis of Impact Signal

Figure 5:
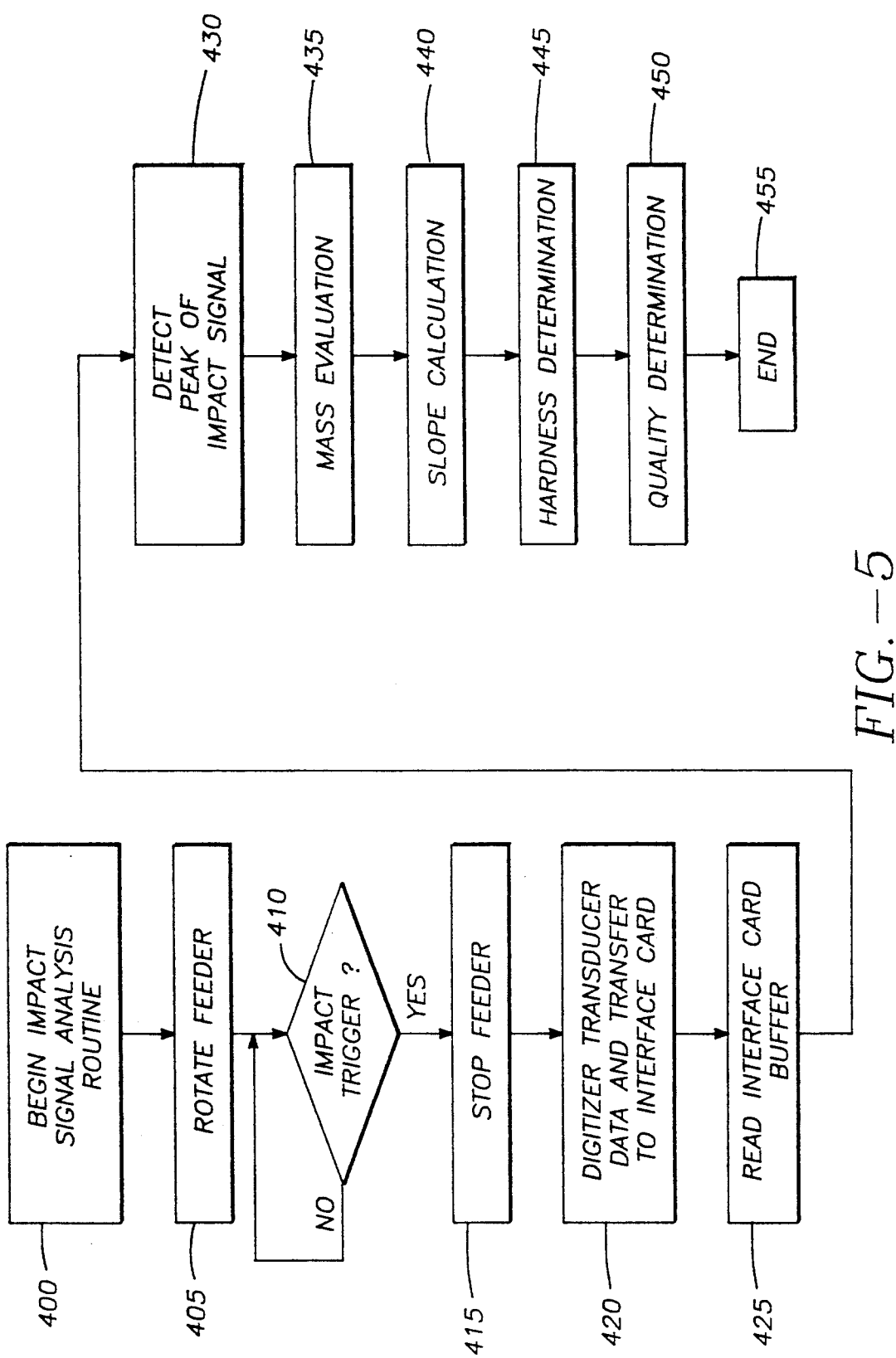
FIG. 5 shows a flow chart of a time-domain impact signal analysis routine.
Figure 6:
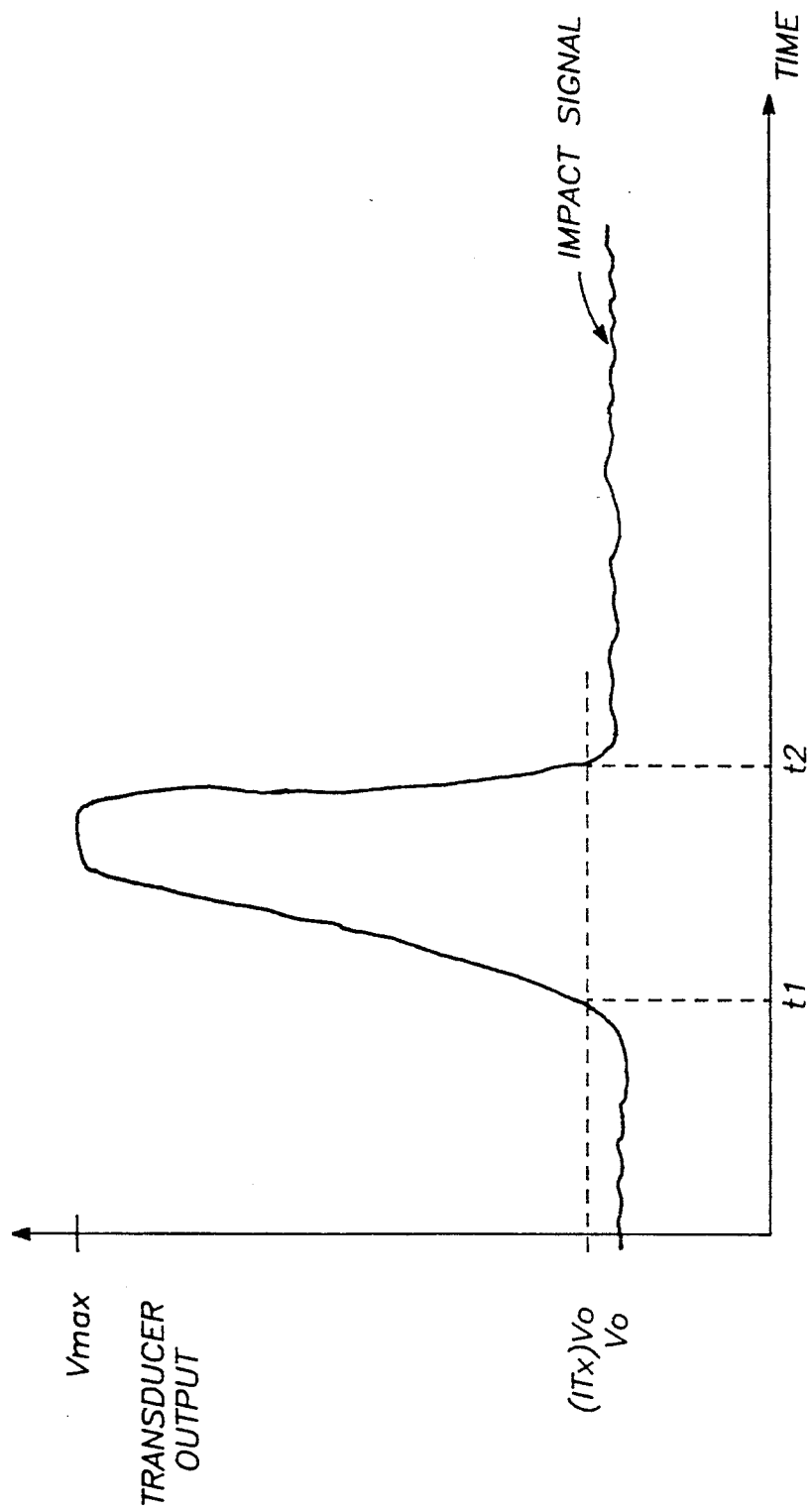
FIG. 6 illustratively represents the electrical output of the impact transducer generated in response to the impact of a soybean thereupon.

FIG. 5 shows a flow chart of the time-domain impact signal analysis routine. Again, the impact signal is generated in response to deflection of a soybean by the impact transducer 80. The analysis routine is commenced (step 400) by rotating (step 405) the feeder disk 160 within the drop tube apparatus 30 until impact of a soybean upon the transducer 80. This impact is detected by monitoring (step 410) the electrical output of the transducer 80 in the manner shown in FIG. 6. As shown in FIG. 6, impact is deemed to occur at time $t_1$ when the electrical output of the transducer 80 rises to a value of $(1+x)VO$, where VO corresponds to the quiescent transducer output signal and the default value of x is 0.1. The feeder disk 160 is then stopped (step 415) and the impact signal is digitized by the interface card 380 (FIG. 4) at a 1 MHz sampling rate (step 420). The initial 1024 samples of the impact signal are then transferred (step 425) from the interface card 380 to the microcomputer. A largest sample value (Vmax) is then identified, and a group of ten sample values centered about the largest value (e.g., the four samples preceding Vmax and the five subsequent samples) are then averaged in order to determine a peak value proportional to soybean mass (step 430). The mass of each soybean may be determined (step 435) by inserting the peak value of the impact signal associated therewith into an empirical relationship stored within the microcomputer. Specifically, an empirical linear equation relating soybean mass to peak impact signal magnitude may be formulated by dropping soybeans of known mass through the drop tube 70 and recording the magnitude of the impact signal corresponding to each.

Again referring to FIG. 6, it has been found that soybean hardness is related to the spread of the impact signal proximate the peak region. This spread corresponds to the time $(t_2-t_1)$ separating the two points at which the impact signal value is equal to $(1+x)VO$. However, since the spread of the impact signal is correlated with mass, hardness may not be uniquely determined solely on the basis of the time differential $t_2-t_1$. Fortunately, it has also been determined that the slope of the impact signal proximate time $t_2$ is proportional to hardness and independent of soybean mass. The slope at time $t_2$ may be found (step 440) by approximating a straight line, hereinafter referred to as the hardness line, based on a set of values of the impact signal between Vmax and the impact signal value of 1.1 VO at time $t_2$. A line-fitting routine such as that described by Press, et al. in *Numerical Recipes—The art of Scientific Computing*, pp. 504–505 may be used to fit this set of values of the impact signal in a minimum sum-of-squares error sense to a straight line corresponding to the hardness line (step 445).

The hardness line may also be used to detect flaws in the internal structure of the soybean. Specifically, it has been found that the minimum sum-of-squares error between the set of signal values used to calculate the hardness line and the hardness line itself is larger for soybeans that are broken, shrivelled, or diseased than for healthy soybeans. It follows that a user-defined quality determination based on any desired combination of soybean mass, hardness and internal structure may be made on the basis of the time-domain analysis of the impact signal (step 450). For example, all soybeans below a certain mass, or those characterized by a sum-of-squares error larger than a predefined threshold, may be classified as unacceptable. The determination of soybean quality based on such a set of user-defined criteria concludes the impact signal analysis routine (step 455).

Digital Image Analysis

Figure 7:
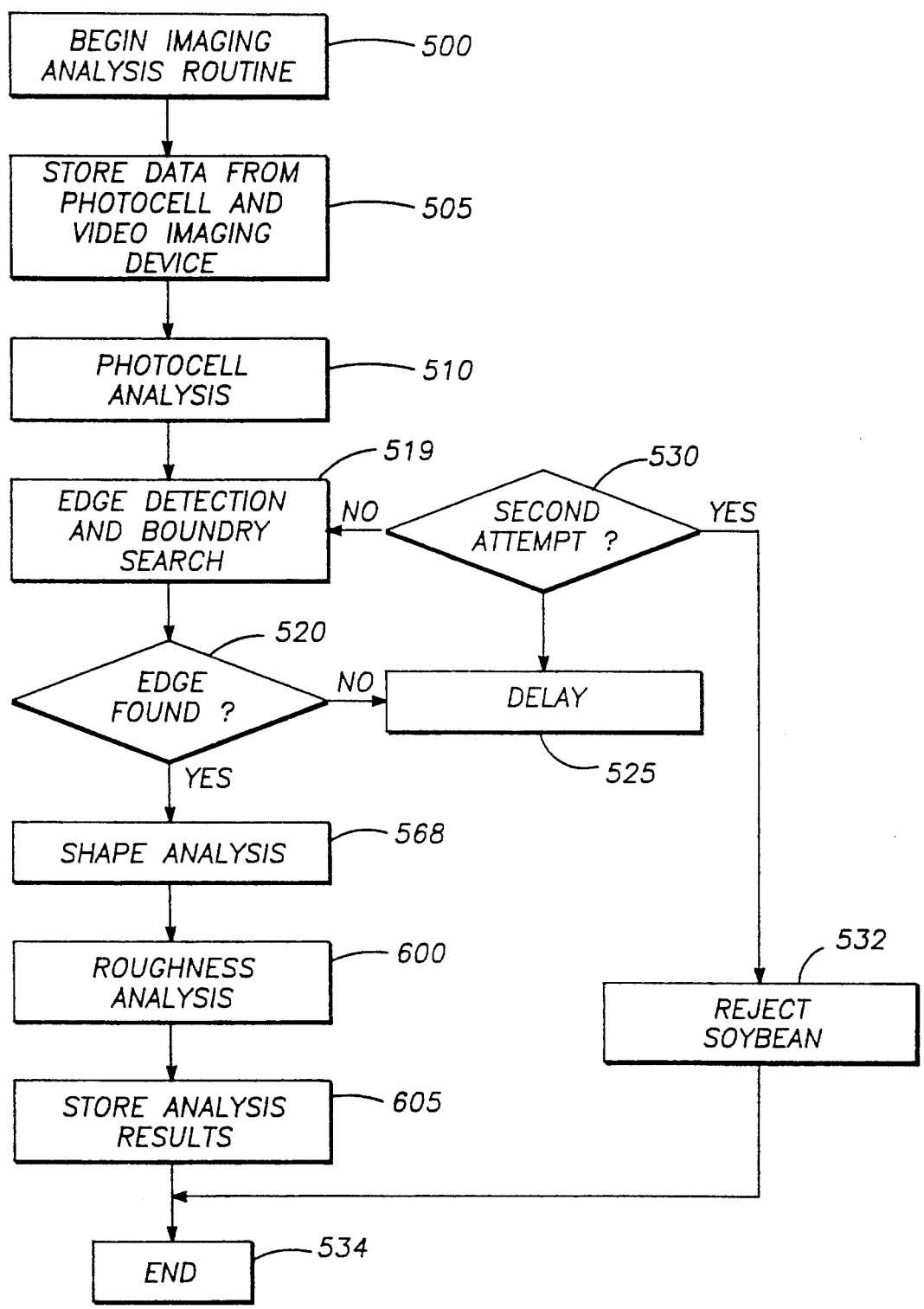
FIG. 7 depicts a flow chart of an imaging analysis routine utilized by the inventive quality determination system.
Figure 8:
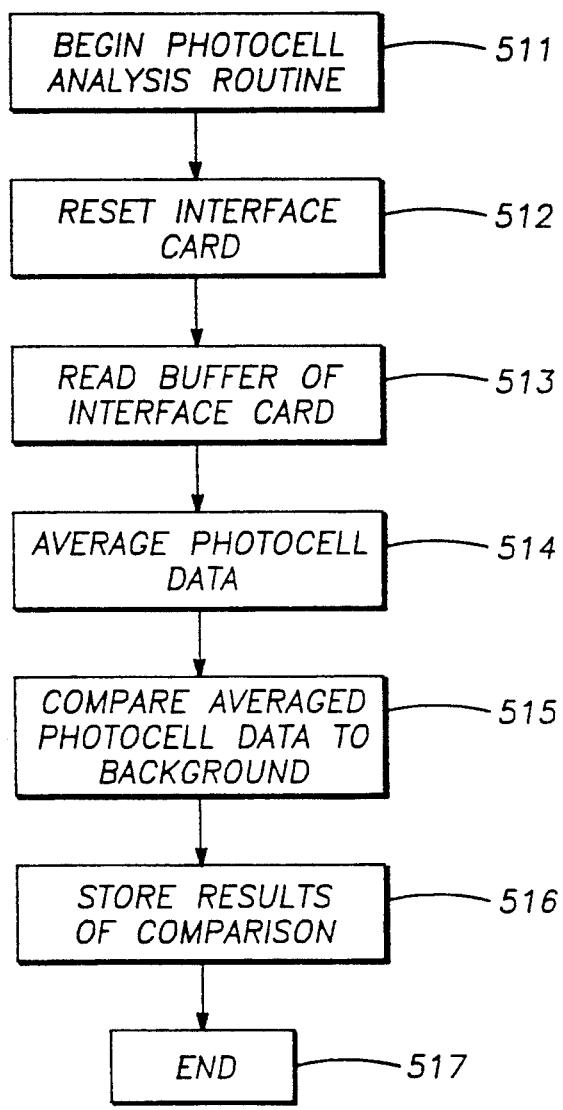
FIG. 8 shows a flow chart illustrating the manner in which a signal generated by a photocell is processed by the present invention.

FIG. 7 depicts a flow chart of the imaging analysis routine conducted subsequent to completion of the impact signal analysis routine. The imaging routine is commenced (step 500) by measuring soybean lustre by processing (step 510) the signal generated by the photocell 270 as shown in FIG. 8. Referring to FIG. 8, the microcomputer initiates (step 511) the photocell analysis routine by resetting (step 512) the interface card 380 (FIG. 4). Again, the photocell 270 is disposed to continuously provide an electrical signal indicative of the amount of radiant energy from the lighting source 250 reflected by the holding bin 100 and by any soybeans therein. The interface card 380 samples the photocell signal, generally at a sampling rate of less than 1 MHz, during an interval immediately following generation of the impact signal. Between one and three hundred samples will typically be stored (step 505) within the channel #1 buffer of the interface card 380. The microcomputer finds the average (steps 513 and 514) of these samples and compares (step 515) the result with a background photocell signal (i.e., the signal produced by photocell 270 when no soybeans are present within the holding bin 100). The results of this comparison are indicative of soybean lustre (reflectivity), and will preferably be stored (steps 516 and 517) within the microcomputer to be used in a subsequent evaluation of soybean quality based on the outcome of the remaining portions of the imaging analysis routine.

Figure 9:
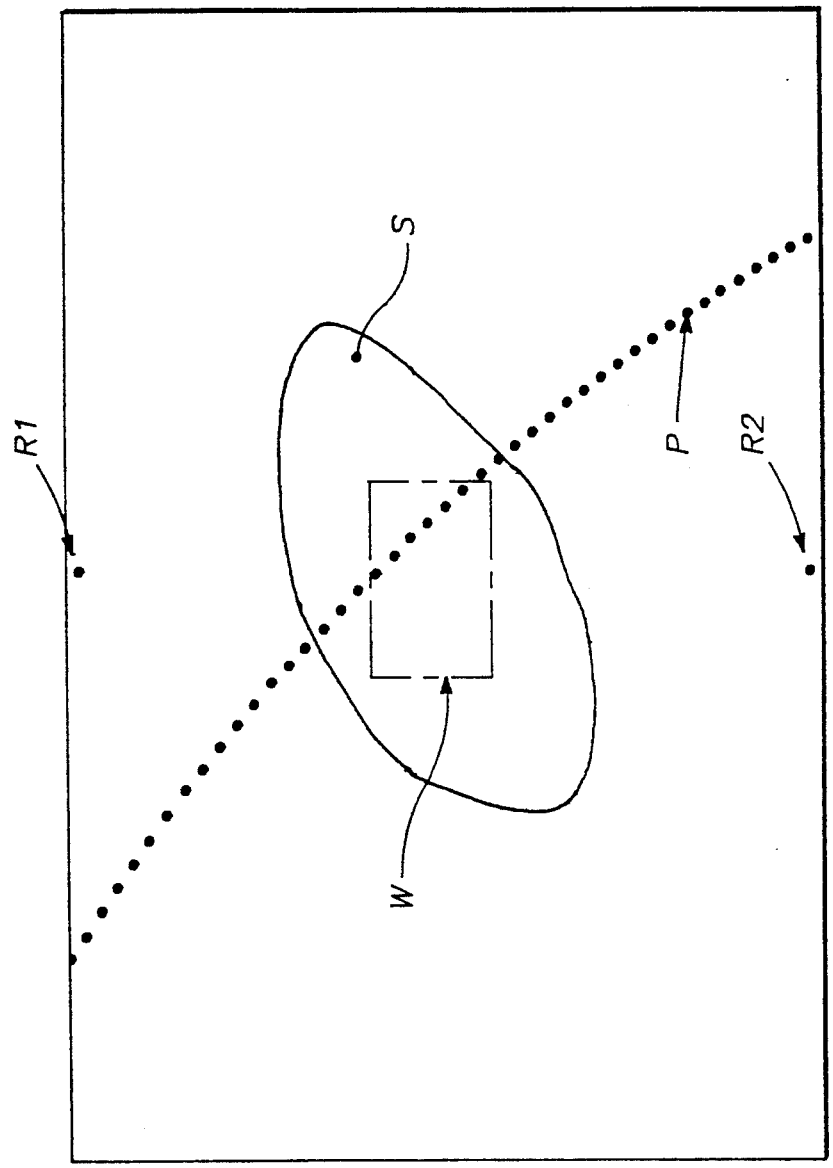
FIG. 9 depicts a simplified illustration of a digital image representation of a field of view encompassed by the imaging device included within the inventive quality determination system.

As is indicated in FIG. 7, the next step (step 519) in the imaging analysis routine involves detecting the entrance of a soybean into the field of view of the imaging device 40. Since the path taken by soybeans falling from the trough 90 into the holding bin 100 may be controlled by varying the angle of the trough 90, a search window within the center of the digital representation generated by the imaging device 40 may be monitored to detect the presence of soybeans. Specifically, FIG. 9 depicts a simplified illustration of a digital image representation of the field of view F of the imaging device 40, in which is included a soybean S and upon which is superimposed a dashed line indicative of the location of a search window W and a dotted line showing the path P of soybean S. A background reference is calculated for each search operation by averaging the values of first and second reference pixels R1 and R2 located proximate the periphery of the field of view F. When the average value of the approximately forty pixel elements within the search window W differs by a predetermined threshold from the background reference, a soybean is deemed to exist within the window W. The microcomputer then sets a flag (step 520) to trigger the edge detection operation (FIG. 7). If a soybean is not found within the search window W, the search operation is repeated until a soybean is located (steps 525, 530, 532 and 534).

FIG. 10 is a flow chart summarizing the manner in which the edge of the soybean S is distinguished from the background of the digital image representation. In particular, the pixel elements located on a vertical line originating at the upper periphery of the field of view F (FIG. 9) proximate reference pixel R1 are sequentially compared (steps 535 and 540) against the background reference. A first point on the edge of the soybean S is considered to have been located (step 545) when the value of a pixel on this vertical line exceeds the background pixel value by a predetermined amount. If the lower boundary of the field of view is reached (step 550) before finding a suitably bright pixel, the program pauses and then makes a second attempt to find the soybean edge. If the second attempt is unsuccessful (step 555) the soybean is rejected as a poor quality bean. The edge detection routine is resumed again when another soybean is detected within the search window W.

Once a first pixel point on the edge of the soybean has been located a boundary search operation is commenced (step 560). During the boundary search process a set of pixel locations located on the boundary of the soybean are accumulated (step 565), thereby allowing the shape of the soybean to be determined (FIG. 7, step 568). The boundary search operation proceeds in a counterclockwise manner around the edge of the soybean, and involves finding the most likely direction of the next boundary pixel relative to the position of the boundary pixel last located. Specifically, FIG. 11 illustratively represents a set of eight direction vectors used in the boundary search operation. Since the search proceeds counterclockwise, after the first edge pixel has been found the value of a test pixel located left (i.e., in direction 2) of the first edge pixel by a search radius is compared with a reference value equal to the value of the first pixel less a predefined number of intensity units. If the value of the test pixel exceeds the background value it is deemed to be the second edge pixel. If the value of the test pixel is not sufficiently large relative to the reference, a second test pixel is identified by finding the pixel located in direction 3 relative to the first pixel, and separated therefrom by a distance approximately equivalent to the search radius. This process is repeated for test pixels at direction vectors 4, 5, 6, ..., etc. until a suitably bright test pixel is found. The search process may be expedited by altering the direction vector initially searched after accumulation of each edge pixel. For example, if the most recent edge pixel found is located in direction 4 relative to the previous edge pixel, direction 3 will first be searched in attempting to locate the next edge pixel. In this way the search process "remembers" the relative location of the previous edge pixel and thus more efficiently tracks the soybean perimeter.

The boundary search operation results in the accumulation (step 570) of a set of pixels which approximate the soybean boundary. The accuracy of the approximation may be increased by reducing the search radius, but such a reduction tends to lengthen the duration of the search process since more boundary points are accumulated. The process terminates when an edge pixel is found within an area of predefined size (e.g., a 4×4 pixel area) relative to the first edge (steps 575 and 580) pixel. Alternatively, the process is aborted (steps 585, 590 and 592) if greater than a maximum number, typically on the order of one-thousand, of edge pixels are accumulated without satisfying the termination criteria mentioned above.

Next, the location of the center of the soybean is calculated (step 595) using the accumulated set of boundary pixels. This calculation may be performed, for example, by finding a major elliptical axis corresponding to the line between the most widely separated pixel locations. The location of the soybean center may be approximated by finding the midpoint of this line.

Figure 12:
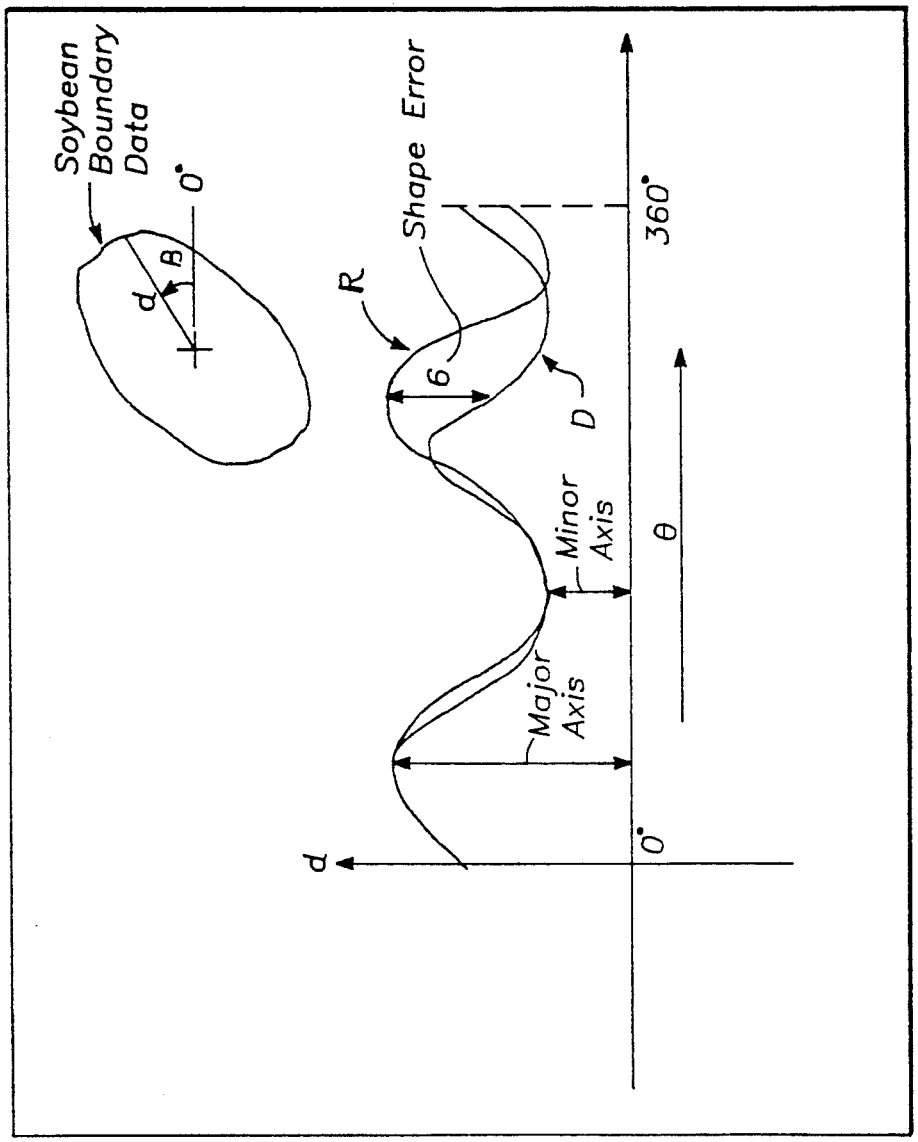
FIG. 12 depicts the manner in which the shape and the boundary roughness of each soybeam may be calculated using an accumulated set of boundary pixels and the location of the center of the soybean.

FIG. 12 depicts the manner in which the shape and surface texture (roughness) of each soybean may be calculated using the accumulated set of boundary pixels and the location of the center of the soybean. Specifically, the boundary defined by the accumulated set of edge pixels is divided into three-hundred sixty parts ($\theta = 0$ to 359 degrees) and the distance "di", i=0 to 359, from the center to each is then calculated. The distance di may then be plotted as a function of the angle $\theta$ as shown by the edge data curve D in FIG. 12. The plot corresponding to a reference ellipse R is superimposed over the curve D by aligning the data point corresponding to the major axis of the reference ellipse with the first peak in the edge data curve D.

The roughness of the soybean may be estimated (see FIG. 7, steps 600 and 605) by computing the variance between the edge data point di and its neighborhood $d_{i+1}$ over $\theta = 0, 1, 2, \ldots, 360$ degrees. Referring to FIG. 12, roughness may be quantified as $\Sigma(d_i - d_{i+1})^2 / 360$, where "i" ranges from 0 to 359. A user may indicate tolerance for roughness by specifying the maximum variance between the curves D and R to be exhibited by accepted soybeans. Similarly, an estimate of the extent to which the shape of the soybean agrees with the reference ellipse R may be obtained by finding the error $\sigma$ between the reference ellipse R and the edge data curve D. Again with reference to FIG. 12, shape error may be quantified as $\Sigma \sigma_i^2/360$, where "i" ranges from 0 to 359. Again, a user may specify the maximum value of shape error to be associated with soybeans of acceptable quality. Finally, an indication of soybean roundness may be obtained by finding the ratio of the minor axis to the major axis.

FIG. 13 depicts the manner in which the texture, area and color of the surface of each soybean may be calculated using a pixel-by-pixel comparison and area normalization. Upon completion of the edge detection routine, a display graphics subroutine is called which superimposes a solid boundary over the set of boundary points. In addition, a calculation box is generated so as to enclose the solid boundary as indicated in FIG. 13. As is discussed below with reference to FIG. 14, a texture analysis program processes pixels from the upper left corner of the calculation box, proceeding from left to right and from top to bottom (see e.g., steps 620, 625, 635, 655, 660, 665 and 670).

Figure 14:
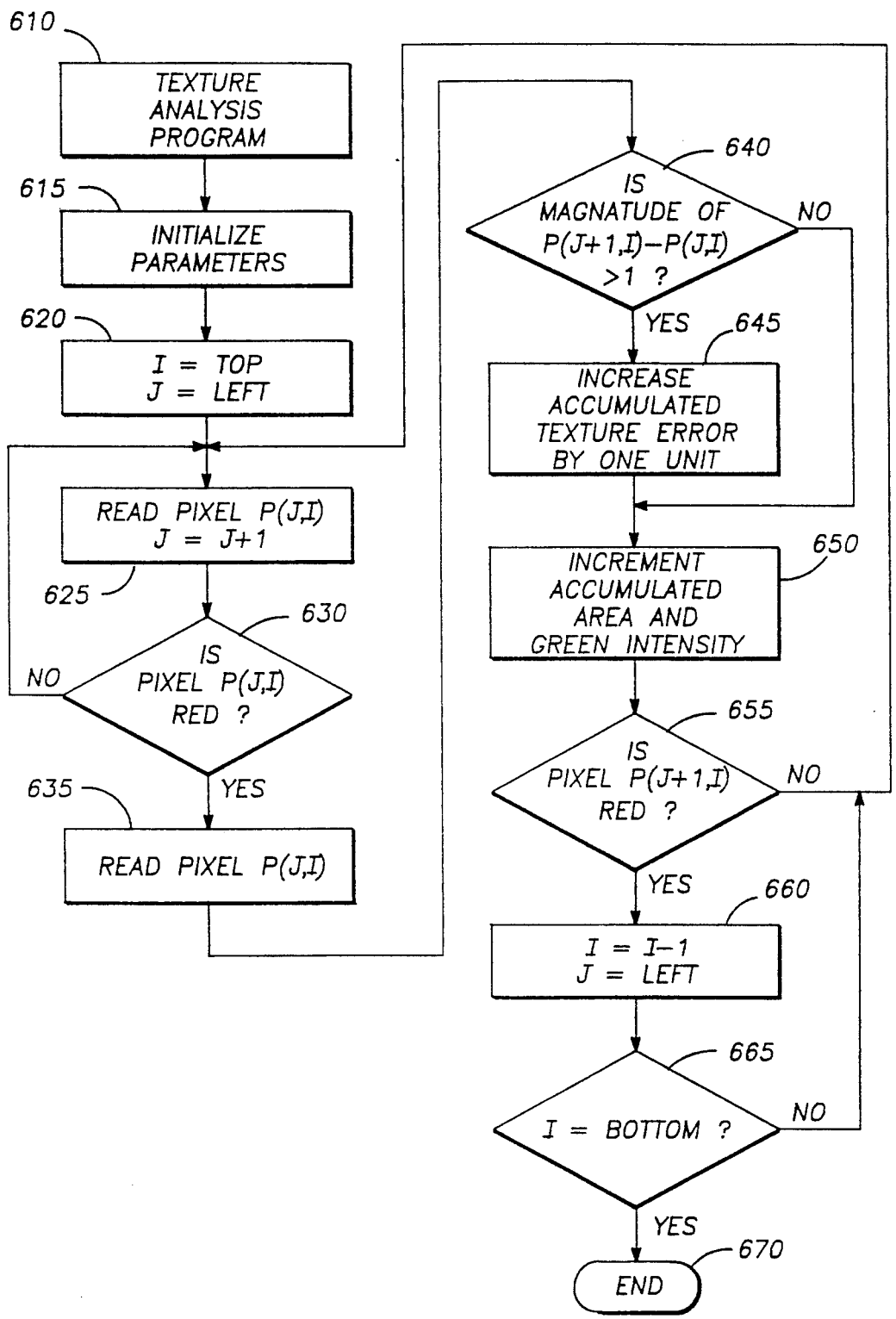
FIG. 14 is a flow chart depicting implementation of a texture analysis program.

FIG. 14 is a flow chart depicting implementation of a texture analysis and color determination program (610). Beginning in the upper left corner (steps 615 and 620) of the calculation box (FIG. 13), the difference in intensity between each pixel and its neighbor to the right is accumulated to produce an aggregate texture error (steps 625, 630, 635, 640 and 645). The texture error is normalized by dividing the aggregate texture error by the surface area of the soybean, wherein the surface area is determined by counting the number of pixels included within the soybean boundary (FIG. 13). The normalized texture error relates to the prevalence of surface defects (e.g., mechanical damage, blemishes, shrivelling, or wrinkling).

A determination of soybean color may be made when the imaging system 40 is implemented with a set of three data buffers disposed to respectively store the red, green and blue intensity of each pixel element. As is indicated by FIG. 14, if a pixel is determined to be green the aggregate green intensity is incremented (650). The aggregate green intensity may then be divided by the surface area of the soybean in order to obtain a normalized green intensity. This normalized value is typically of more utility than red or blue intensity given that the color of soybeans is generally some shade of yellow.

Soybeans are routed by the rejection device 50 into the accepted and rejected bins 120 and 130 on the basis of the quality determinations made in regard to the impact signal and imaging analysis routines. If either analysis routine indicates that a soybean is of unacceptable quality, the soybean is deposited in rejected soybean bin 130. It is emphasized, however, that a user may specify the extent to which each measured physical parameter contributes to the overall quality assessment made by each analysis routine.

While the present invention has been described with reference to a few specific embodiments, the description is illustrative of the invention and is not to be construed as limiting the invention. Various modifications may occur to those skilled in the art without departing from the true spirit and scope of the invention as defined by the appended claims. For example, the teachings of the present invention may also be applied to various other agricultural products such as different varieties of beans and legumes.

What is claimed is:

1. An apparatus for determining quality of an agricultural product, comprising:

acoustical transducer means for generating a transducer signal indicative of a set of physical characteristics of said product;

imaging means for synthesizing a digital image representation of said product; and signal processing means for analyzing said transducer signal and said digital image representation;

whereby, based on said analysis, a degree of quality is associated with said agricultural product.

2. The apparatus of claim 1 wherein said acoustical transducer means further includes a drop tube feeder apparatus for dropping said agricultural product upon said transducer.

3. The apparatus of claim 2 wherein said imaging means includes camera means for providing an image of said agricultural product and for digitizing said image so as to create said digital image representation.

4. The apparatus of claim 1 wherein said physical characteristics include mass and hardness.

5. The apparatus of claim 4 wherein said digital image representation includes information pertaining to shape and boundary roughness of said agricultural product.

6. The apparatus of claim 5 wherein said signal processing means includes means for determining said shape of said agricultural product based on said digital image representation, said shape determining means including means for identifying a portion of said digital image representation as corresponding to an edge of said agricultural product and means for determining a center of said product relative to said edge.

7. The apparatus of claim 6 wherein said signal processing means includes means for determining roughness of said agricultural product by plotting separation between predefined sections of said edge and said center and comparing said plot with a reference plot.

8. The apparatus of claim 4 wherein said acoustical transducer means includes an impact transducer, said transducer signal being generated in response to impact of said agricultural product upon said transducer.

9. The apparatus of claim 8 wherein said signal processing means includes means for performing a time-domain analysis of said transducer signal.

10. The apparatus of claim 9 wherein said time-domain analysis means includes means for detecting a peak region of said transducer signal, wherein magnitude of said transducer signal at said peak region corresponds to said mass of said agricultural product.

11. The apparatus of claim 10 wherein a slope of said peak signal at a predefined magnitude thereof corresponds to said hardness of said agricultural product.

12. An apparatus for quality determination of beans, comprising:

acoustical transducer means for generating a transducer signal indicative of mass and hardness of said beans, said transducer means having a drop tube feeder apparatus coupled to an impact transducer;

imaging means for synthesizing a digital image representation of said product, said digital image representation including information pertaining to at least one characteristic from the set of bean characteristics consisting of shape, texture, area and color; and signal processing means for performing a time-domain analysis upon said transducer signal and for analyzing said digital image representation;

whereby, based on said time-domain analysis and upon said analysis of said digital image representation, degrees of quality are associated with said beans.

13. A method for determining quality of an agricultural product comprising the steps of:
dropping said product upon an impact transducer, said transducer being disposed to generate a transducer signal indicative of a set of physical characteristics of said product;
creating an image of said product;
digitizing said image so as to create a digital image representation of said product;
storing said digital image representation in computer memory;
analyzing said transducer signal and digital image representation in accordance with predefined criteria;
whereby, based on said analysis, a degree of quality is associated with said agricultural product.

14. The method of claim 13 wherein said digital image representation includes information pertaining to at least one characteristic included within the set of product characteristics consisting of surface texture, area and color.

15. The method of claim 13 wherein said step of analyzing includes the step of determining said shape of said agricultural product based on said digital image representation, said shape determining step including the steps of:
identifying a portion of said digital image representation as corresponding to an edge of said agricultural product, and
determining a center of said product relative to said edge.

16. The method of claim 15 wherein said step of analyzing includes the step of determining boundary roughness of said agricultural product by plotting separation between predefined sections of said edge and said center and comparing said plot with a reference plot.

17. The method of claim 16 wherein said agricultural product comprises a bean.

18. The method of claim 13 wherein said physical characteristics include mass and hardness.

19. The method of claim 18 wherein said digital image representation includes information pertaining to shape and boundary roughness of said agricultural product.

20. The method of claim 19 wherein said step of analyzing includes the step of performing a time-domain analysis upon said transducer signal.

21. The method of claim 20 wherein said time-domain analysis step includes the step of detecting a peak region of said transducer signal, wherein magnitude of said transducer signal at said peak region corresponds to said mass of said agricultural product.

22. The method of claim 21 wherein said time-domain analysis step includes the step of determining the slope of said transducer signal at a predefined magnitude thereof wherein said slope corresponds to said hardness of said agricultural product.

* * * * *

UNITED STATES PATENT AND TRADEMARK OFFICE
CERTIFICATE OF CORRECTION

PATENT NO. :   5,309,374

DATED      :   May 3, 1994

INVENTOR(S) :  Misra et al.

It is certified that error appears in the above-identified patent and that said Letters Patent is hereby corrected as shown below:

column 2, line 64, change "reals" to --realms--.

column 8, line 2, delete "(step 435)".

column 8, line 2, after "inserting" insert --(step 435)--.

column 10, line 30, delete "(steps 575 and 580)".

column 10, line 31, after "pixel" insert --(steps 575 and 580)--.

Signed and Sealed this

Twenty-seventh Day of September, 1994

Attest:

BRUCE LEHMAN

Attesting Officer        Commissioner of Patents and Trademarks